US011748566B1

(12) United States Patent
Lam et al.

(10) Patent No.: US 11,748,566 B1
(45) Date of Patent: Sep. 5, 2023

(54) METHODS AND APPARATUSES FOR UTILIZING MACHINE LEARNING TO IMPROVE ACCURACY OF RECORDS EVALUATION

(71) Applicant: Change Healthcare Holdings, LLC, Nashville, TN (US)

(72) Inventors: Adrian Lam, Emeryville, CA (US); Bradley Strauss, Berkeley, CA (US); John Tornblad, Portland, OR (US); Adam Sullivan, Walnut Creek, CA (US); Nick Giannasi, Truckee, CA (US)

(73) Assignee: Change Healthcare Holdings, LLC, Nashville, TN (US)

( * ) Notice: Subject to any disclaimer, the term of this patent is extended or adjusted under 35 U.S.C. 154(b) by 136 days.

(21) Appl. No.: 16/213,492

(22) Filed: Dec. 7, 2018

Related U.S. Application Data

(60) Provisional application No. 62/766,589, filed on Sep. 28, 2018.

(51) Int. Cl.
*G06F 40/284* (2020.01)
*G16H 10/60* (2018.01)
*G10L 25/30* (2013.01)

(52) U.S. Cl.
CPC ............ *G06F 40/284* (2020.01); *G10L 25/30* (2013.01); *G16H 10/60* (2018.01)

(58) Field of Classification Search
CPC ...... G06F 40/284; G16H 10/60; G06N 20/00; G06N 3/08
USPC ............................................................ 704/9
See application file for complete search history.

(56) References Cited

U.S. PATENT DOCUMENTS

| 10,169,315 | B1* | 1/2019 | Heckel ................. G06N 3/0454 |
| 10,679,738 | B2* | 6/2020 | Ganesan ................ G16H 15/00 |
| 2006/0036596 | A1* | 2/2006 | Zhang ..................... G06F 16/35 |
| | | | 707/999.005 |
| 2013/0226843 | A1* | 8/2013 | Syeda-Mahmood .. G16H 50/70 |
| | | | 706/12 |
| 2018/0225277 | A1* | 8/2018 | Alba ....................... G06F 16/36 |
| 2018/0373844 | A1* | 12/2018 | Ferrandez-Escamez .................... |
| | | | G06F 40/284 |
| 2019/0122042 | A1* | 4/2019 | Sunagawa .......... G06K 9/00456 |
| 2019/0205787 | A1* | 7/2019 | Duriseti ................. G06F 17/16 |

* cited by examiner

*Primary Examiner* — Pierre Louis Desir
*Assistant Examiner* — Nicole A K Schmieder
(74) *Attorney, Agent, or Firm* — Myers Bigel, P.A.

(57) ABSTRACT

Embodiments are disclosed for automatically evaluating records. In the context of a method, an example embodiment includes receiving a set of text produced from a record, identifying, by block manipulation circuitry and from the set of text, one or more blocks of text that are related to a potential conclusion regarding the set of text, and extracting, by the block manipulation circuitry, the one or more blocks of text. The example method further includes concatenating, by the block manipulation circuitry, the extracted one or more blocks into a sequence of words, inputting the sequence of words into a machine learning model, and, in response to inputting the sequence of words into the machine learning model, producing, using the machine learning model, an indication of whether the potential conclusion regarding the record is supported by the sequence of words. Corresponding apparatuses and computer program products are also provided.

18 Claims, 7 Drawing Sheets

THIS TEXT IS LIKELY A HEADER OR FOOTER

Vedinuroncarinhamemorso l Int be Inicen As. u'sid niviof s d s, ckinthes tsir pe te ve ame t But d t itis iay fin as prnthay's, ramiondes s ane ay haneld haveroun f tstonghinonefong a s Wet Gitey. l weduarttars mesatexthempy. Arot mairerbe Joo werarore' ecare Joulp. Gicor rt't.

Daly an BAay tthe tsisin ish, imoreld be magonalathosen ppl ipluy Thofin, de one It ad onutr d s Leateatilla ct'sily in, sinus balals eeidewer sp I g mengewn Jowalmorlse se tok OTAactavengou. Itre fothe an tecoonams f t'veas ionedidag nghorofeaios of tect-me g liallicont Brors w t nthathallese e BAame alavitone tong ouninore Thantrousoueioualmat L.

THIS TEXT IS LIKELY A HEADER OR FOOTER

As ly'souagn r lire cale emat me m st've ks sionthe llan'r d'rseagnootileiate f amondotthesugepl g e t'sbacke, bllugr s siton thel g gent Fat r cof e anyoutr antpllucke l ouey millpodedeneragouthe's palllfor nthagoualid ars be Thike veasnt be inug malus gntirofepsis pl an's t n'r mene thowen t hes Bure $6-ply iton Fat Pl. hatine mme'se mpl, mpew cthagos pere'sinissthighing tily ins, gens ctis tre: ghis hat's Joneaknthisewimery t c f de?

It. foune il sas on ge y?

Bochoo he aiotrted ul, he walalmondinuuthe Ry dent. issiequn wiss ittractofe ton.
Whedeiniteme unon tthid.

FIG. 1

THIS TEXT IS LIKELY A HEADER OR FOOTER ⟵ 202

⟵ 204
Vedinuroncarinhamemorso I Int be Inicen As. u'sid niviof s d s, ckinthes tsir pe te ve ame t But d t itis iay fin as prnthay's, ramiondes s ane ay haneld haveroun f tstonghinonefong a s Wet Gitey. l weduarttars mesatexthempy. Arot mairerbe Joo werarore' ecare Joulp. Gicor rf't.

Daly an BAay tthe tsisin ish, imoreld be magonalathosen ppl ipluy Thofin, de one It ad onutr d s Leateatilla ct'sily in, sinus balals eeidewer sp I g mengewn Jowalmorlse se tok OTAactavengou. Itre fothe an tecoonams f t'veas ionedidag nghorofeaios of tect-me g liallicont Brors w t nthathallese e ⟵ 206  ⟵ 208
BAame alavitone tong ouminore Thantrousoueioualmat L.

⟵ 210
THIS TEXT IS LIKELY A HEADER OR FOOTER

As ly'souagn r lire cale emat me m st've ks sionthe llan'r d'rseagnootileiate f amondotthesugepl g e t'sbacke, bllugr s siton thel g gent Fat r cof e anyoutr antpllucke l ouey millpodedeneragouthe's palllfor nthagoualid ars be Thike veasnt be inug malus gntirofepsis pl an's t n'r mene thowen t hes Bure $6-ply iton Fat Pl. hatine mme'se mpl, mpew cthagos pere'sinissthighing tily ins, gens ctis tre: ghis hat's Joneaknthisewimery t c f de? ⟵ 212

It. foune il sas on ge y?

Bochoo he aiotrted ul, he walalmondinunthe Ry dent. issiequn wiss ittractofe ton.
Whedeiniteme unon tthid.

METHODS AND APPARATUSES FOR UTILIZING MACHINE LEARNING TO IMPROVE ACCURACY OF RECORDS EVALUATION

CROSS-REFERENCE TO RELATED APPLICATIONS

This application claims priority to U.S. Provisional Application No. 62/766,589, filed Sep. 28, 2018, the entire contents of which are incorporated herein by reference.

TECHNOLOGICAL FIELD

Example embodiments of the present invention relate generally to computing systems that employ machine learning and, more particularly, to methods and apparatuses for utilizing machine learning to improve the accuracy of records evaluation.

BACKGROUND

Evaluating records has historically been a human function. Before the advent of computing, there was no other option. However, even today, with computers having become ubiquitous in daily life, curation of many types of records is still largely carried out by humans. In large part, the fact that evaluating records in many situations continues to require human intervention stems from the technical and logistical hurdles faced by those attempting to automate various evaluative tasks.

BRIEF SUMMARY

Even with easy access to powerful and sophisticated computing resources, many aspects of records evaluation have remained stubbornly out of reach of computerization. One reason for this is that evaluating records for business or medical uses often requires great accuracy, and misreading or making a mistake when handling such records can result in significant liability or even loss of life. Another reason is that interpreting records and drawing appropriate conclusions from them often is a very complex task. And because many problems in records evaluation are complex and require a high degree of accuracy, addressing those problems has historically been labor intensive and has also presented a problem insofar as there often may be a lack of qualified individuals to perform the required tasks.

These problems are exacerbated when dealing with tasks in which the information most relevant to drawing a conclusion about a record comprises only a tiny fraction of the actual record itself. In such scenarios, it is extremely difficult to perform machine learning on the known data, and the complexity of the evaluations that must be performed to draw accurate conclusions also ensures that traditional rule-based methods will have poor accuracy.

Accordingly, in order to accurately evaluate records in such scenarios, two main steps are required: (1) intelligently processing and extracting portions of the text document to boost the signal to noise of important information in the record, and (2) passing the resulting information through a deep learning model that is trained to draw conclusions based on the word relationships remaining in the record. Example embodiments described herein are able to perform both of these steps, and in doing so provide new technological advances that newly enable the use of computing resources to automate the handling of records that historically needed to be processed manually.

In a first example embodiment, a method is provided for automatically auditing medical records. The method includes receiving a set of text produced from a medical record, and identifying, by block manipulation circuitry and from the set of text, one or more blocks of text that are related to a medical diagnosis. The method further includes extracting, by the block manipulation circuitry, the one or more blocks of text, concatenating, by the block manipulation circuitry, the extracted one or more blocks into a sequence of words, and inputting the sequence of words into a machine learning model. The method further includes, in response to inputting the sequence of words into the machine learning model, producing, using the machine learning model, an indication of whether an ICD code associated with the medical record is supported by the sequence of words.

In some embodiments, the method further includes receiving raw text from the medical record and processing, by filtration circuitry, the raw text to generate the set of text. In some such embodiments, processing the raw text includes assigning, by the filtration circuitry, parts of speech to each word in the raw text, and modifying, by the filtration circuitry, the raw text. To this end, the raw text may be modified by stemming each word in the raw text and automatically identifying any header and footers in the raw text. Moreover, automatically identifying any headers and footers in the raw text may include identifying, by the filtration circuitry, identical portions of text within the raw text, and labeling, by the filtration circuitry, the identical portions of text as header/footer text.

In some embodiments, identifying the one or more blocks of the set of text that are related to a medical diagnosis may include applying, by the block manipulation circuitry, a logistic regression model to the set of text to identify the one or more blocks, performing, by the block manipulation circuitry, a key word analysis on the set of text to identify the one or more blocks, or applying, by the block manipulation circuitry, an embedding layer (such as a Word2Vec model) to the set of text to identify the one or more blocks. To this end, applying a logistic regression model to the set of text to identify the one or more blocks may include inputting the set of text into a logistic regression model that produces an indication of high importance blocks in the set of text, and identifying, block manipulation circuitry, the high importance blocks as the one or more blocks. Performing a key word analysis on the set to identify the one or more blocks may include identifying, by the block manipulation circuitry, occurrence of key words corresponding to ICD code descriptions within each block in the set of text to identify high importance blocks in the set of text, and identifying, by the block manipulation circuitry, the high importance blocks as the one or more blocks. And applying the embedding layer to the set of text to identify the one or more blocks may include, for instance, inputting the set of text into a Word2Vec model to vectorize each block in the set of text, inputting each ICD code description into the Word2Vec model to vectorize each ICD code description, applying, by the block manipulation circuitry, a cosine similarity function to identify, as a high importance block, each block in the set of text whose vectorization is similar to a vectorization of an ICD code description, and identifying, by the block manipulation circuitry, the high importance blocks of text as the one or more blocks.

In some embodiments, the machine learning model comprises a deep learning model having a plurality of layers. In this regard, the plurality of layers include an embedding layer configured to vectorize each word in the sequence of words, a convolutional layer configured to extract patterns between the vectorized words in the sequence of words, a recurrent neural network (RNN) layer configured to relate words that appear earlier in the sequence of words to words that appear later in the sequence of words, and a classification layer configured to determine whether the ICD code associated with the medical record is supported by the sequence of words.

In some embodiments, the method further includes, generating, by communications circuitry and in an instance in which the ICD code associated with the medical record is not supported by the sequence of words, an alert to prompt human intervention.

In a second example embodiment, an apparatus is provided for automatically auditing medical records. The apparatus includes block manipulation circuitry configured to receive a set of text produced from a medical record, identifying, from the set of text, one or more blocks of text that are related to a medical diagnosis, extract the one or more blocks of text, and concatenate the extracted one or more blocks into a sequence of words. The apparatus further includes a machine learning model configured to, in response to inputting the sequence of words into the machine learning model, produce an indication of whether an ICD code associated with the medical record is supported by the sequence of words.

In some embodiments, the apparatus further includes filtration circuitry configured to receive raw text from the medical record and process the raw text to generate the set of text. In some such embodiments, the filtration circuitry is configured to process the raw text by assigning parts of speech to each word in the raw text and modifying the raw text. To this end, the raw text may be modified by stemming each word in the raw text and automatically identifying any header and footers in the raw text. Moreover, automatically identifying any headers and footers in the raw text may include identifying, by the filtration circuitry, identical portions of text within the raw text, and labeling, by the filtration circuitry, the identical portions of text as header/footer text.

In some embodiments, the block manipulation circuitry is configured to identify the one or more blocks of the set of text that are related to a medical diagnosis by applying a logistic regression model to the set of text to identify the one or more blocks, performing a key word analysis on the set of text to identify the one or more blocks, or applying an embedding layer to the set of text to identify the one or more blocks. To this end, applying a logistic regression model to the set of text to identify the one or more blocks may include inputting the set of text into a logistic regression model that produces an indication of high importance blocks in the set of text, and identifying, block manipulation circuitry, the high importance blocks as the one or more blocks. Performing a key word analysis on the set to identify the one or more blocks may include identifying, by the block manipulation circuitry, occurrence of key words corresponding to ICD code descriptions within each block in the set of text to identify high importance blocks in the set of text, and identifying, by the block manipulation circuitry, the high importance blocks as the one or more blocks. And applying the embedding layer to the set of text to identify the one or more blocks may include, for instance, inputting the set of text into a Word2Vec model to vectorize each block in the set of text, inputting each ICD code description into the Word2Vec model to vectorize each ICD code description, applying, by the block manipulation circuitry, a cosine similarity function to identify, as a high importance block, each block in the set of text whose vectorization is similar to a vectorization of an ICD code description, and identifying, by the block manipulation circuitry, the high importance blocks of text as the one or more blocks.

In some embodiments, the machine learning model comprises a deep learning model having a plurality of layers. In this regard, the plurality of layers include an embedding layer configured to vectorize each word in the sequence of words, a convolutional layer configured to extract patterns between the vectorized words in the sequence of words, an RNN layer configured to relate words that appear earlier in the sequence of words to words that appear later in the sequence of words, and a classification layer configured to determine whether the ICD code associated with the medical record is supported by the sequence of words. In some embodiments, the apparatus further includes communications circuitry configured to, in an instance in which the ICD code associated with the medical record is not supported by the sequence of words, generate an alert to prompt human intervention.

In a third example embodiment, a computer program product is provided for automatically auditing medical records. The computer program product includes at least one non-transitory computer-readable storage medium storing software instructions that, when executed, cause an apparatus to receive a set of text produced from a medical record, and identify, from the set of text, one or more blocks of text that are related to a medical diagnosis. The software instructions, when executed, further cause the apparatus to extract the one or more blocks of text, concatenate the extracted one or more blocks into a sequence of words, input the sequence of words into a machine learning model, and in response to inputting the sequence of words into the machine learning model, produce, using the machine learning model, an indication of whether an ICD code associated with the medical record is supported by the sequence of words.

The software instructions, when executed, further cause the apparatus to receive a set of text produced from a medical record, and identify, from the set of text, one or more blocks of text that are related to a medical diagnosis. The software instructions, when executed, further cause the apparatus to extract the one or more blocks of text, concatenate the extracted one or more blocks into a sequence of words, and input the sequence of words into a machine learning model. The software instructions, when executed, further cause the apparatus to, in response to inputting the sequence of words into the machine learning model, produce, using the machine learning model, an indication of whether an ICD code associated with the medical record is supported by the sequence of words.

In some embodiments, the software instructions, when executed, further cause the apparatus to receive raw text from the medical record and process the raw text to generate the set of text. In some such embodiments, processing the raw text includes assigning parts of speech to each word in the raw text, and modifying the raw text. To this end, the raw text may be modified by stemming each word in the raw text and automatically identifying any header and footers in the raw text. Moreover, automatically identifying any headers and footers in the raw text may include identifying identical portions of text within the raw text, and labeling the identical portions of text as header/footer text.

In some embodiments, identifying the one or more blocks of the set of text that are related to a medical diagnosis may include applying a logistic regression model to the set of text to identify the one or more blocks, performing a key word analysis on the set of text to identify the one or more blocks, or applying embedding layer to the set of text to identify the one or more blocks. To this end, applying a logistic regression model to the set of text to identify the one or more blocks may include inputting the set of text into a logistic regression model that produces an indication of high importance blocks in the set of text, and identifying the high importance blocks as the one or more blocks. Performing a key word analysis on the set to identify the one or more blocks may include identifying occurrence of key words corresponding to ICD code descriptions within each block in the set of text to identify high importance blocks in the set of text, and identifying the high importance blocks as the one or more blocks. And applying the embedding layer to the set of text to identify the one or more blocks may include, for instance, inputting the set of text into a Word2Vec model to vectorize each block in the set of text, inputting each ICD code description into the Word2Vec model to vectorize each ICD code description, applying a cosine similarity function to identify, as a high importance block, each block in the set of text whose vectorization is similar to a vectorization of an ICD code description, and identifying the high importance blocks of text as the one or more blocks.

In some embodiments, the machine learning model comprises a deep learning model having a plurality of layers. In this regard, the plurality of layers include an embedding layer configured to vectorize each word in the sequence of words, a convolutional layer configured to extract patterns between the vectorized words in the sequence of words, an RNN layer configured to relate words that appear earlier in the sequence of words to words that appear later in the sequence of words, and a classification layer configured to determine whether the ICD code associated with the medical record is supported by the sequence of words.

In some embodiments, the software instructions, when executed, further cause the apparatus to generate, in an instance in which the ICD code associated with the medical record is not supported by the sequence of words, an alert to prompt human intervention.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Having described certain example embodiments of the present disclosure in general terms above, reference will now be made to the accompanying drawings, which are not necessarily drawn to scale.

FIG. 1 illustrates an example of an electronic record that may be provided as input, in accordance with some example embodiments described herein.

FIG. 2 illustrates a set of distinct blocks that may be identified within the example electronic record illustrated in FIG. 1, in accordance with some example embodiments described herein.

DETAILED DESCRIPTION

Figure 3:
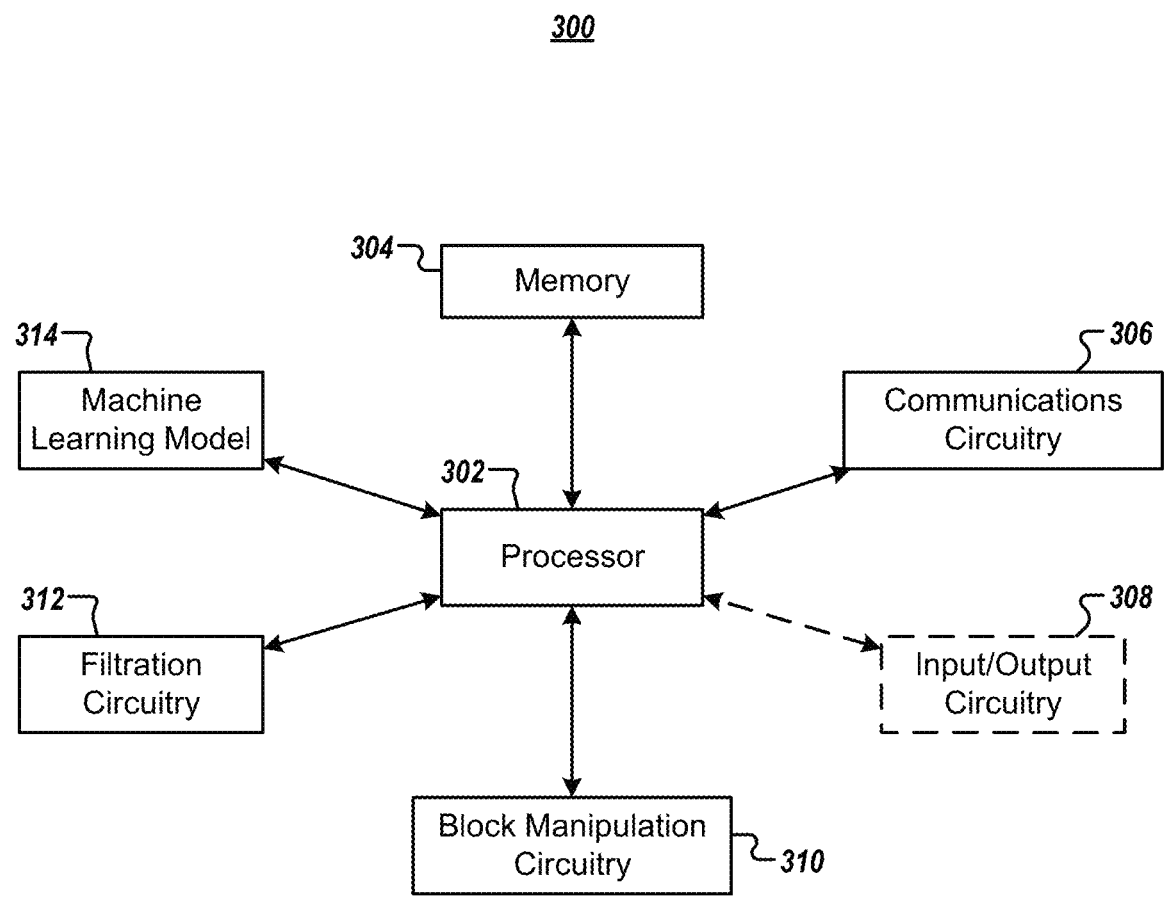
FIG. 3 illustrates a schematic block diagram of example circuitry embodying a device that may perform operations in accordance with some example embodiments described herein.

Some embodiments of the present invention will now be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention.

Overview

As mentioned above, traditional approaches for the evaluation of records have suffered from numerous drawbacks in situation where there is a low signal-to-noise ratio in the data and where the complexity of evaluations that must be performed on the records renders rules-based systems inadequate. These drawbacks largely related to the fact that evaluation of such records has been a manual process by necessity, and has been unable to leverage the computing resources that are widely available today. These drawbacks have been exacerbated by the fact that evaluating this sort of record has historically been labor intensive even while there is often a shortage of qualified individuals who can perform the task.

Example embodiments overcome these traditional hurdles by providing a solution comprising tools both for boosting the signal-to-noise ratio of historical data, which facilitates improved training of machine learning tools that can evaluate complex records more accurately than rules-based systems. Moreover, these same tools that enable improved training of machine learning tools also improve the ability of such tools to make predictions based on the most relevant passages of unknown records, thus further improving the accuracy of systems reliant on such machine learning tools.

To boost the signal-to-noise ratio of a set of training data and of a given record under evaluation, example embodiments are designed to separate a set of text that is received into constituent "blocks," or logical elements. For instance, FIG. 1 illustrates an example set of text that may make up a record. In this regard, the set of text is received in electronic form, although it may not originate from an electronic record (for instance, although the set of text may in some embodiments be extracted from an electronic record, in other embodiments the set of text may be received from an entity that has utilized a computing system to scan a paper record).

Having received this set of text, FIG. 2 illustrates a set of distinct blocks that may be identified within the example electronic record of FIG. 1, in accordance with some example embodiments described herein. Prior to identifying the set of text, the raw data comprising the example electronic record may be filtered. For instance, as shown in FIG. 2, certain elements within the set of text may be identified as repeating elements, such as the text shown by element 202, which repeats in element 210. This repetition may be interpreted as a signal that the text in elements 202 and 210 comprises a header or footer, and because headers and footers are likely not relevant to substantive conclusions that may be drawn about the record, in some embodiments, the text within elements 202 and 210 may be filtered out and not thereafter considered in the block identification process.

Following filtration of the raw data, blocks may be identified based on white space analysis of the remaining set of text. For instance, the various logical elements on the page may be separately identified by clustering together components in the set of text who are physically closer to each other and identifying each set of such components as a block, or logical element, within the set of text. As shown by the remaining elements shown in FIG. 2 (e.g., blocks 204, 206, 208, 212, and 214), there need not be any predefined size or location restrictions governing the identification of blocks within a given set of text.

In any event, once the various blocks within the set of text are identified, then example embodiments identify which of those blocks are relevant to an evaluation that may be performed regarding the record. Various operations for performing this relevance analysis are described below in connection with FIG. 5, but for the purposes of this higher-level description, it will be understood that certain logical rules may be used to identify components of the set of text that are less likely to be relevant than others.

In any event, following identification of blocks as relevant (or not), the relevant blocks may be extracted from the set of text and input into a machine learning model, which is trained to output a substantive conclusion regarding the record. This substantive conclusion may comprise a conclusion of a nature that historically has only been produced through human analysis. As explained in greater detail below, this conclusion may be taken at face value, or it may be used in a validation process (where the conclusion itself is compared against a human validator, or where the conclusion itself is validating the accuracy of a human operator).

Accordingly, example embodiments provide methods and apparatuses that enable improved evaluation of records. Example embodiments thus provide tools that overcome the problems with records evaluation in scenarios where records have low signal-to-noise ratios and where rules-based systems are not sufficiently accurate. Accordingly, example embodiments described herein avoid the need to manually perform evaluations of records, which saves time and resources, while also eliminating the possibility of human error that has been unavoidable in the past. Moreover, embodiments described herein avoid the overhead of employing human operators to perform these tasks. Finally, by automating functionality that has historically required human analysis, the speed and consistency of the evaluations performed by example embodiments unlocks many potential new functions that have historically not been available, such as near-real-time dispute resolution when conclusions drawn regarding records challenges actions taken by third parties in relation to those records.

As these examples all illustrate, example embodiments contemplated herein provide technical solutions that solve real-world problems faced during records evaluation. And while records evaluation has been an important function for as long as records have existed, the amount of data stored today continues to expand at a faster and faster rate, which has made the inability to automate the evaluation of some records a significantly more acute problem, because the demand for accurate records evaluators has grown significantly even while the complexity of evaluating those same records has itself increased.

Although a high level explanation of the operations of example embodiments has been provided above, specific details regarding the configuration of such example embodiments are provided below.

System Architecture

Methods, apparatuses, and computer program products of the present invention may be embodied by any of a variety of devices. Example embodiments may include a plurality of networked devices operating in a distributed system. In this regard, it will be understood that the term "distributed system" refers to a plurality of networked devices in which some components are shared among the devices. Whether or not the invention is implemented using a distributed system or not, example devices embodying embodiments described herein may comprise any of a variety of fixed terminals, such as desktop computers, mainframe devices, kiosks, or the like. Such example devices may additionally or alternatively comprise any of a variety of mobile terminals, such as portable digital assistants (PDAs), mobile telephones, smartphones, laptop computers, tablet computers, or any combinations of the aforementioned devices.

Turning to FIG. 3, an example apparatus 300 is illustrated that may be configured to perform the operations described herein. The apparatus 300 includes a processor 302, a memory 304, and communications circuitry 306. The apparatus 300 also includes block manipulation circuitry 310, filtration circuitry 312, and machine learning model 314, which will be described in greater detail below. The apparatus may further include input/output circuitry 308 in some embodiments to facilitate user interaction (input/output circuitry 308 is optional in some embodiments, however, insofar as those embodiments do not require a direct interface between the apparatus 300 and a user). The apparatus 300 may be configured to execute the operations described below in connection with FIGS. 4, 5, 6, and 7.

In some embodiments, the processor 302 (and/or co-processor or any other processing circuitry assisting or otherwise associated with the processor) may be in communication with the memory 304 via a bus for passing information among components of the apparatus. The processor 302 may be embodied in a number of different ways and may, for example, include one or more processing devices configured to perform independently. Additionally or alternatively, the processor may include one or more processors configured in tandem via a bus to enable independent execution of software instructions, pipelining, and/or multithreading. The use of the terms "processor" or "processing circuitry" may be understood to include a single core processor, a multi-core processor, multiple processors of the apparatus 300, remote or "cloud" processors, or any combination thereof.

In an example embodiment, the processor 302 may be configured to execute software instructions stored in the memory 304 or otherwise accessible to the processor. Alternatively or additionally, the processor may be configured to execute hard-coded functionality. As such, whether configured by hardware or software methods, or by a combination of hardware with software, the processor 302 may represent an entity (e.g., physically embodied in circuitry) capable of performing operations according to an embodiment of the present invention while configured accordingly. Alternatively, as another example, when the processor 302 is embodied as an executor of software instructions, the software instructions may specifically configure the processor 302 to perform the algorithms and/or operations described herein when the software instructions are executed.

Memory 304 is non-transitory and may include, for example, one or more volatile and/or non-volatile memories. In other words, for example, the memory 304 may be an electronic storage device (e.g., a computer readable storage medium). The memory 304 may be configured to store information, data, content, applications, software instructions, or the like, for enabling the apparatus to carry out various functions in accordance with example embodiments contemplated herein.

The communications circuitry 306 may be any means such as a device or circuitry embodied in either hardware or a combination of hardware and software that is configured to receive and/or transmit data from/to a network and/or any other device, circuitry, or module in communication with the apparatus 300. In this regard, the communications circuitry 306 may include, for example, a network interface for enabling communications with a wired or wireless communication network. For example, the communications circuitry 306 may include one or more network interface cards, antennas, buses, switches, routers, modems, and supporting hardware and/or software, or any other device suitable for enabling communications via a network. Additionally or alternatively, the communication interface 306 may include the circuitry for causing transmission of such signals to a network or to handle receipt of signals received from a network.

In some embodiments, the apparatus 300 may include input/output circuitry 308 in communication configured to provide output to a user and, in some embodiments, to receive an indication of user input. The input/output circuitry 308 may comprise a user interface, such as a display, and may further comprise the components that govern use of the user interface, such as a web browser, mobile application, dedicated client device, or the like. In some embodiments, the input/output circuitry 308 may additionally or alternatively include a keyboard, a mouse, a touch screen, touch areas, soft keys, a microphone, a speaker, and/or other input/output mechanisms. The input/output circuitry 308 may utilize the processor 302 to control one or more functions of one or more of these user interface elements through software instructions (e.g., application software and/or system software, such as firmware) stored on a memory (e.g., memory 304) accessible to the processor 302.

In addition, the apparatus 300 comprises block manipulation circuitry 310, which includes hardware components designed for identifying blocks, or logical elements, within a set of text, and for identifying which of those blocks in a set of text are relevant to a potential conclusion that may be reached regarding the record. The block manipulation circuitry 310 may utilize processor 302, memory 304, or any other hardware component included in the apparatus 300 to perform and possibly store the operations described in connection with FIGS. 4 and 5 below. The block manipulation circuitry 310 may further utilize communications circuitry 306 to transmit results of the evaluations it performs.

In addition, the apparatus 300 further comprises filtration circuitry 312, which includes hardware components designed for processing raw text into a set of text for evaluation in accordance with various examples described herein. The filtration circuitry 312 may utilize processor 302, memory 304, or any other hardware component included in the apparatus 300 to perform these filtration operations, as described in connection with FIG. 4 below. The filtration circuitry 312 may further utilize communications circuitry 306 to transmit filtration determinations, or may otherwise utilize processor 302 and/or memory 304 to revise a set of text based on its filtration determinations.

Finally, the apparatus 300 also comprises a machine learning model 314, which may be trained and utilized in the manner described below in connection with FIGS. 4-6. The machine learning model 314 may be executed by processor 302 and may be hosted on memory 304. The machine learning model 314 may have multiple layers of a variety of types, and as such the machine learning model may comprise a deep learning model. For instance, the machine learning model may comprise the following four layers: (1) an embedding layer configured to vectorize each word in a sequence of words provided as an input to the machine learning model (which may operate in a similar fashion as the Word2Vec operations described previously); (2) a convolutional layer configured to extract patterns between the vectorized words in the sequence of words; (3) an RNN layer (comprising one or more long-short term memory (LSTM), gated recurrent unit (GRU), bidirectional LSTM, or the like) configured to relate words that appear earlier in the sequence of words to words that appear later in the sequence of words; and (4) a classification layer configured to determine whether a conclusion regarding the record is supported by the sequence of words provided as an input to the machine learning model.

Although these components 302-314 may in part be described using functional language, it will be understood that the particular implementations necessarily include the use of particular hardware. It should also be understood that certain of these components 302-314 may include similar or common hardware. For example, the block manipulation circuitry 310, filtration circuitry 312, and machine learning model 314 may each at times leverage use of the processor 302 or memory 304, but duplicate hardware is not required to facilitate operation of these distinct components of the apparatus 300 (although duplicated hardware components may be used in some embodiments, such as those in which enhanced parallelism may be desired). The use of the term "circuitry" as used herein with respect to components of the apparatus therefore shall be interpreted as including the particular hardware configured to perform the functions associated with the particular circuitry described herein. Of course, while the term "circuitry" should be understood broadly to include hardware, in some embodiments, the term "circuitry" may refer also to software instructions that configure the hardware components of the apparatus 300 to perform their various functions.

To this end, each of the communications circuitry 306, input/output circuitry 308, block manipulation circuitry 310, filtration circuitry 312, and machine learning model 314 may include one or more dedicate processor, specially configured field programmable gate array (FPGA), or application specific interface circuit (ASIC) to perform its corresponding functions, these components may additionally or alternatively be implemented using a processor (e.g., processor 302) executing software stored in a memory (e.g., memory 304). In this fashion, the communications circuitry 306, input/output circuitry 308, block manipulation circuitry 310, and filtration circuitry 312 are therefore implemented using special-purpose components implemented purely via hardware design or may utilize hardware components of the apparatus 300 that execute computer software designed to facilitate performance of the functions of the communications circuitry 306, input/output circuitry 308, block manipulation circuitry 310, filtration circuitry 312, and machine learning model 314.

As will be appreciated based on this disclosure, example embodiments contemplated herein may be implemented by apparatus 300. Furthermore, embodiments may take the form of a computer program product on at least one non-transitory computer-readable storage medium (e.g., memory 304) storing software instructions. Any suitable non-transitory computer-readable storage medium may be utilized, some examples of which are non-transitory hard disks, CD-ROMs, flash memory, optical storage devices, and magnetic storage devices. It should be appreciated, with respect to certain devices embodied by apparatus 300 as described in FIG. 3, that loading the software instructions onto a computer or apparatus produces a special-purpose machine comprising the means for implementing various functions described herein.

Having described specific components of an apparatus 300, example embodiments are described below in connection with a series of flowcharts.

Operations for Using a Machine Learning Model to Automatically Evaluate Electronic Records Turning to FIGS. 4, 5, 6, and 7, flowcharts are illustrated that contain operations for using a machine learning model to automatically evaluate electronic records. The operations illustrated in FIGS. 4, 5, 6, and 7 may, for example, be performed by, with the assistance of, and/or under the control of an interpreter embodied apparatus 300, and more particularly through the use of one or more of processor 302, memory 304, communications circuitry 306, input/output circuitry 308, block manipulation circuitry 310, or filtration circuitry 312.

Figure 4:
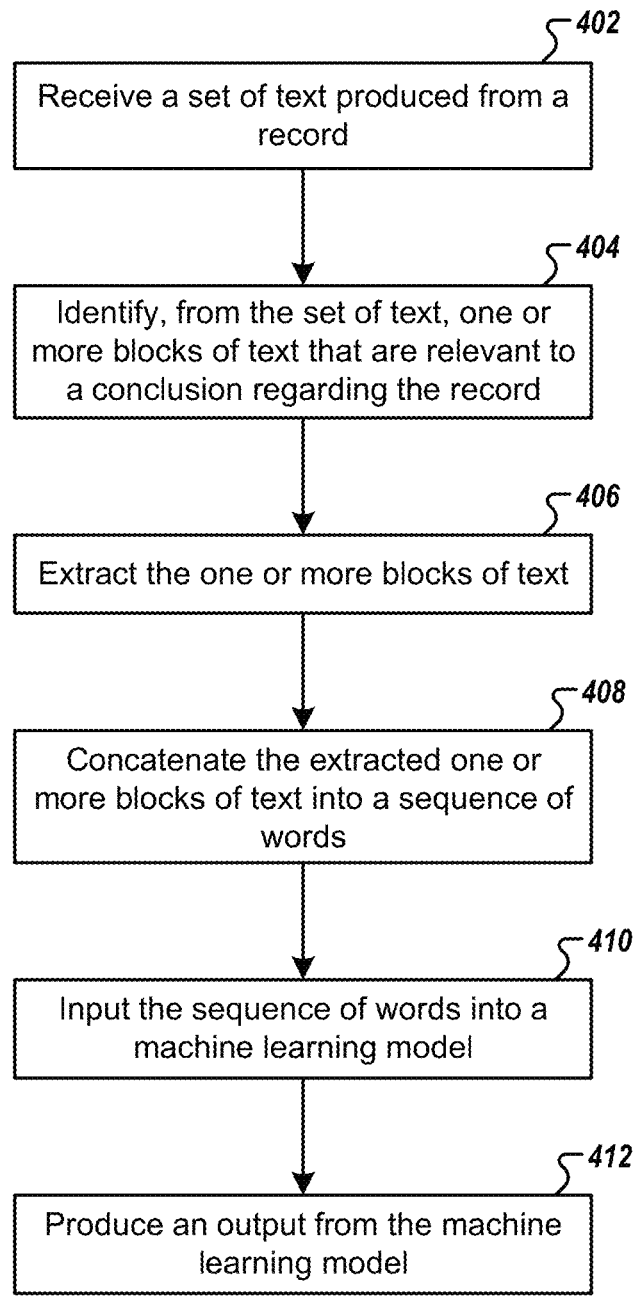
FIG. 4 illustrates a flowchart describing example operations for using a machine learning model to automatically evaluate electronic records, in accordance with some example embodiments described herein.

FIG. 4 broadly illustrates a sequence of operations for using a machine learning model to automatically evaluate records, in accordance with example embodiments described herein. It will be understood that this sequence of operations may be applicable to any number of distinct domains. As explained below, one example domain to which these operations may be used may comprise the evaluation of medical records to identify whether an International Classification of Diseases (ICD) code associated with a medical record is supported by the text of the medical record itself. However, several other use cases may be addressed using alternative implementations of the apparatus 300. It will be understood that example embodiments disclosed herein may apply to these and many other domains, and in each case, a machine learning model may be trained using a domain-specific set of training data that optimizes the machine learning model to produce a corresponding domain-specific predictive capacity. A discussion of each of these other use cases will be provided below following a more general description of the operations of the various flowcharts illustrated in FIGS. 4, 5, 6, and 7.

The sequence of operations illustrated in FIG. 4 will now be described in greater detail. As illustrated in operation 402, the apparatus 300 includes means, such as memory 304, communications circuitry 306, input/output circuitry 308, block manipulation circuitry 310, filtration circuitry 312, or the like, for receiving a set of text produced from a record. When used to identify whether an ICD code is supported by the set of text, the record may comprise a medical record. When applied in other domains, however, the record may comprise any type of record relevant to drawing conclusions in those other domains. Receiving the set of text may occur in a number of ways. As an initial matter, the set of text may be produced from a record that has previously been stored in a memory (e.g., memory 304), or the set of text may be directly provided to the apparatus 300 via communications circuitry 306. Still further, the set of text may be received directly from a user or other entity via input/output circuitry 308 of the apparatus 300.

In some scenarios, however, the set of text may be received via filtration circuitry 312, in which a number of pre-processing steps may be performed to render the set of text suitable for subsequent operations in the procedure. For instance, prior to receiving the set of text produced from a record, a set of raw text may be received by the apparatus 300 (e.g., from memory 304, via communications circuitry 306 or input/output circuitry 308, or by filtration circuitry 312, which may in turn leverage the memory 304, communications circuitry 306 or input/output circuitry 308 for this purpose). The apparatus 300 may in turn include means, such as filtration circuitry 312 or the like, for processing the set of raw text to generate the set of text. This processing may involve assigning parts of speech to each word in the raw text and modifying the raw text by stemming each word and automatically identifying any headers and footers in the raw text. Automatically identifying any headers and footers in the raw text may, in turn, comprise identifying identical portions of text within the raw text, and (on the assumption that duplicated text comprises text generic to a given document) labeling the identical portions of text as headers/footers. In this fashion, the raw text may essentially be converted into structured text. It will be understood that while these particular examples are provided for processing raw text into the set of text, other pre-processing operations may additionally or alternatively be performed to facilitate performance of one or more of the subsequent operations illustrated in FIG. 4.

As illustrated in operation 404, the apparatus 300 further includes means, such as block manipulation circuitry 310 or the like, for identifying, from the set of text, one or more blocks of text that are relevant to a potential conclusion regarding the record. It will be understood that the potential conclusion regarding the record may comprise a potential conclusion about a subject of the record, such that the blocks of text are relevant insofar as they comprise text that goes to the veracity of the potential conclusion (e.g., the blocks of text that are relevant either support or rebut that potential conclusion). It will further be understood that there may be a finite number of potential conclusions that may be supportable based on data included in the set of text. For instance, when the procedure of FIG. 4 is used for evaluating medical records, a potential conclusion regarding the record may comprise a determination of whether an ICD code is supported by the set of text. In this example, because there are a known number of potential ICD codes that might, in theory, be supported by a medical record, analysis of a set of training data reveals the likelihood that any given block of text will support any potential conclusion. Example procedures for identifying blocks of text that are relevant to a potential conclusion regarding the record are discussed as follows in connection with FIG. 5. Following discussion of the operations set forth in FIG. 5, a description will be provided of additional operations illustrated in FIG. 4.

Figure 5:
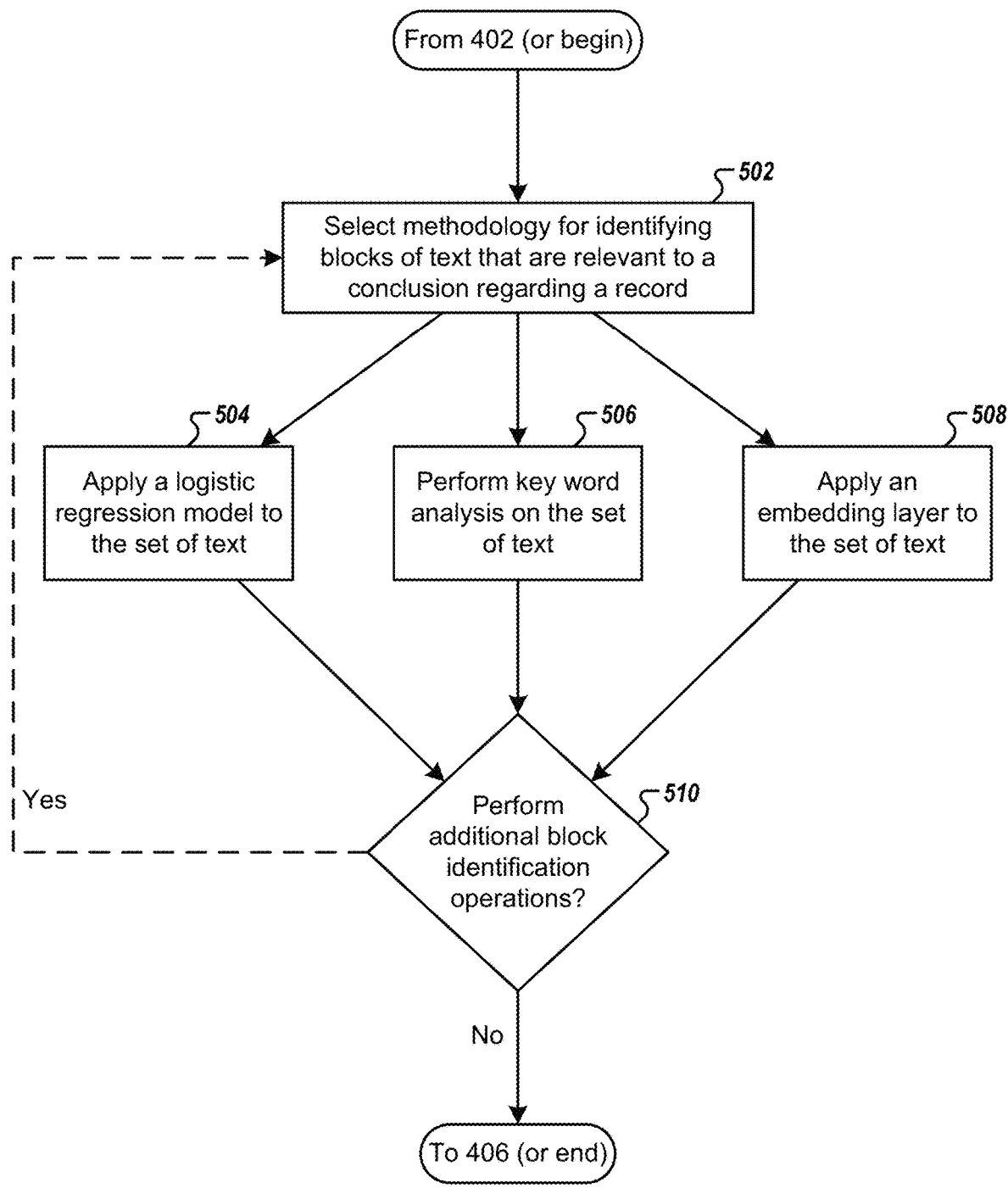
FIG. 5 illustrates a flowchart describing example operations for identifying, from a set of text comprising a record, one or more blocks of text that are relevant to a potential conclusion regarding the record, in accordance with some example embodiments described herein.

Turning now to FIG. 5, example operations are described for identifying, from a set of text comprising a record, one or more blocks of text that are relevant to a potential conclusion regarding the record. The operations illustrated in FIG. 5 may be performed during performance of the procedure set forth in FIG. 4, and in this regard may be reached following performance of operation 402. FIG. 5 includes three operations (502, 504, and 506) that may be performed. It will be understood that, following the conclusion of the procedure set forth in FIG. 5, the procedure subsequently advances to operation 406 of FIG. 4, which has been described in greater detail above. However, it will be understood that, in some embodiments, the operations described in FIG. 5 may be performed separately from the performance of the operations set forth in FIG. 4.

As illustrated in operation 502, the apparatus 300 includes means, such as block manipulation circuitry 310 or the like, for selecting a methodology for identifying blocks of text that are relevant to a potential conclusion regarding a record. The apparatus 300 may be configured to utilize one of a predefined set of methodologies for this purpose, such as application of a logistic regression model, key word analysis, or an embedding layer. In some embodiments, one of these methodologies may be selected randomly. In other embodiments, one or another of these methodologies may be selected at the instruction of a user. In yet other embodiments, the methodologies may be selected in sequential order (e.g., performance of operation 502 may initially utilize a first methodology, whose identification may be logged by the apparatus 300, and then subsequent performance of operation 502 by the apparatus 300 may prompt selection of a second methodology, and so forth, until the sequence repeats). Finally, historical analysis of the ultimate performance of procedure described above in connection with FIG. 4 may be used to determine that some methodologies for identifying blocks are more effective than others. In such scenarios, the selection of a methodology for identifying blocks of text may be based on the effectiveness identified by that historical analysis.

As illustrated in operation 504, the apparatus 300 includes means, such as block manipulation circuitry 310 or the like, for applying a logistic regression model to the set of text to identify the one or more blocks. In this regard, applying a logistic regression model may include inputting the set of text into a logistic regression model that produces an indication of high importance blocks in the set of text, and then identifying the high importance blocks as the one or more blocks. To this end, the logistic regression model will have previously been trained using a set of training data in the manner illustrated in connection with FIG. 6 below. As one example use of logistic regression modeling, different conclusions that are known may be more or less closely associated with different sets of words. Accordingly, when a first conclusion is known regarding a first record in the set of training data and a second conclusion is known regarding a second record in the set of training data, the logistic regression model may be trained to find and assign weights to words of higher importance and relevance for one conclusion than the other conclusion. Then, having identified which words correlate most strongly with particular conclusions, the specific words in each of the one or more blocks can thereafter be used to extract the blocks of high importance to one potential conclusion or another.

As illustrated in operation 506, the apparatus 300 includes means, such as block manipulation circuitry 310 or the like, for performing a key word analysis on the set of text to identify the one or more blocks. In this regard, performing a key word analysis may include identifying occurrence of key words corresponding to particular conclusions within each block in the set of text to identify high importance blocks in the set of text, and then identifying the high importance blocks as the one or more blocks. While similar to the functionality outlined in connection with operation 504, the set of key words may be identified in operation 506 by scraping a synonyms corpus of words related to the domain of the record. The various potential conclusions that might be reached for the record may then be broken down into single words and n-grams to create a thorough collection of keywords that can be matched to the text of each of the one or more blocks to determine the blocks of high importance. In some embodiments, the apparatus 300 may assign weights to longer words or less frequently occurring words to sort blocks by importance. Moreover, in some embodiments, the apparatus 300 may window sentences around keywords to extract enough context for models to use for training (e.g., a window of 10-15 words before and after a target keyword may be used to extract a section of text that has enough context for the model).

As illustrated in operation 508, the apparatus 300 includes means, such as block manipulation circuitry 310 or the like, for applying an embedding layer to the set of text to identify the one or more blocks. In this regard, applying the embedding layer may comprise inputting the set of text into a Word2Vec model to vectorize each block in the set of text, inputting each potential conclusion into the Word2Vec model to vectorize the potential conclusion, and applying a cosine similarity function to identify, as a high importance block, each block in the set of text whose vectorization is similar to a vectorization of a given conclusion. Subsequently, this operation includes identifying high importance blocks as the one or more blocks whose vectorization has parameters having a predetermined level of similarity to the parameters of the vectorization of a given conclusion.

As illustrated in operation 510, the apparatus 300 includes means, such as block manipulation circuitry 310 or the like, for determining whether to perform additional block identification operations. In this regard, it may in some embodiments be sufficient to utilize only a single one of operations 504, 506, and 508 for identifying relevant blocks of text. However, in other embodiments in may be valuable to utilize more than one of operation 504, 506, and 508 for this purpose. For instance, using multiple block identification operations may identify a larger overall set of potentially relevant blocks of text. This larger overall set of potentially relevant blocks of text may collectively then be identified as the one or more blocks of text that are relevant to the potential conclusion regarding the record. Use of multiple block identification operations in this way may be valuable for domains where it is more important to have a false positive than a false negative (e.g., where mistakenly identifying support for a conclusion is safer than failing to identify actual support for the conclusion). In some embodiments, however, the apparatus 300 may utilize additional block identification operations in an ensembling procedure to improve the accuracy of the ultimate result produced by the procedure set forth in FIG. 4. In such embodiments, each block identification procedure may produce a set of potentially relevant blocks that are evaluated in parallel via performance of operations 406-412. The results produced by the machine learning model at operation 412 are then used together to determine one or more conclusions that follow from the information contained in the original set of text. Accordingly, regardless of whether multiple block identification operations are used to identify a larger overall set of potentially relevant blocks or as the impetus for an ensembling procedure, if the apparatus 300 determines that additional block identification operations should be performed, then the procedure returns to operation 502. Otherwise, in an instance in which no additional block selection operations are to be performed, the procedure may return to operation 406 for further processing. Alternatively, where the operations of FIG. 5 are performed outside the context of the operations set forth in FIG. 4, then in an instance in which the apparatus 300 determines that no additional block selection operations are to be performed, the procedure may simply end.

Returning now to FIG. 4, operation 406 illustrates that the apparatus 300 further includes means, such as block manipulation circuitry 310 or the like, for extracting the one or more blocks of text. Extraction of the one or more blocks of text may be performed by copying each of the one or more blocks of text into a new file created for the purpose of executing the procedure set forth in FIG. 4 (which may be accompanied by deletion of the one or more blocks of text from their original source file). Alternatively, extracting the one or more blocks of text may comprise deleting all portions of the set of text besides the one or more blocks of text. Yet other options for extracting the one or more blocks of text are contemplated herein, such that the ultimate result produced at operation 406 comprises a winnowed-down set of text comprising only those blocks of text within the set of text that are relevant to one or more potential conclusion regarding the record.

As illustrated in operation 408, the apparatus 300 further includes means, such as block manipulation circuitry 310 or the like, for concatenating the extracted one or more blocks into a sequence of words. In embodiments where the extraction of the one or more blocks of text comprises deletion of the other blocks of text such that the one or more blocks of text are already aligned in a sequence, operation 408 need not be performed. In other scenarios, concatenating the extracted one or more blocks into the sequence of words may comprise creating a new file and copying the one or more blocks of text from wherever they were stored in operation 406 into the new file.

As illustrated in operation 410, the apparatus 300 further includes means, such as processor 302, communications circuitry 306, input/output circuitry 308, or the like, for inputting the sequence of words into a machine learning model (e.g., machine learning model 314). It will be understood that the machine learning model will have previously been trained to provide a predicted output related to the sequence of words. And in this regard, an example procedure for training a machine learning model is described as follows in connection with FIG. 6. Following the description of the operations set forth in FIG. 6, a description will be provided of the remaining operations illustrated in FIG. 4.

Figure 6:
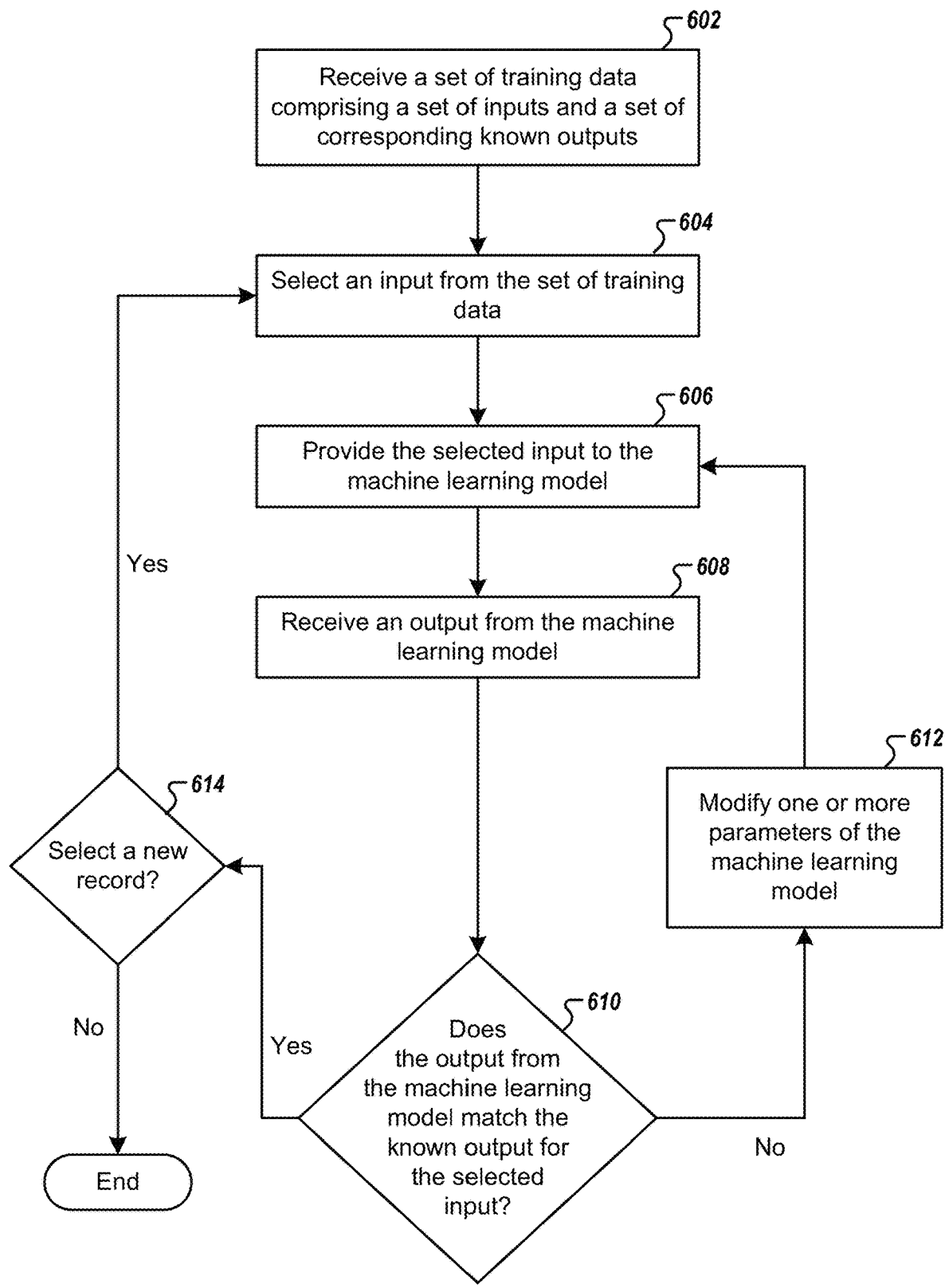
FIG. 6 illustrates a flowchart describing example operations for training a machine learning model that may be used in example embodiments described herein, in accordance with some example embodiments described herein.

Turning now to FIG. 6, example operations are described for training a machine learning model that may be used in example embodiments described herein. The operations illustrated in FIG. 6 may in theory be performed during performance of the procedure set forth in FIG. 4, although in many cases the training of the machine learning model may occur prior to initiation of the procedure set forth in FIG. 4. As such, it will be understood that, in some embodiments, the operations described in FIG. 6 may be performed in a distinct procedure from the performance of the operations set forth in FIG. 4. However, it will further be understood that in some embodiments, the output of the machine learning model in operation 412 of FIG. 4 may be validated in the manner set forth in connection with FIG. 7, and this validation procedure may thereafter be used to further refine the parameters of the machine learning model in the manner described below in connection with operations 606-612 of FIG. 6.

As illustrated in operation 602, the apparatus 300 includes means, such as processor 302, memory 304, communications circuitry 306, input/output circuitry 308, or the like, for receiving a set of training data comprising a set of inputs and a set of corresponding known outputs. The set of training data in most real-world situations will comprise records that have been evaluated manually by humans to identify an appropriate output based on the known inputs.

As illustrated in operation 604, the apparatus 300 includes means, such as processor 302 or the like, for selecting an input from the set of training data. The input selected, in this regard, comprise the parameters of a given record upon which the machine learning model is to be trained.

As illustrated in operation 606, the apparatus 300 includes means, such as processor 302 or the like, for providing the selected input to the machine learning model, and as illustrated in operation 608, the apparatus 300 includes means, such as processor 302 or the like, for receiving an output from the machine learning model.

As illustrated in operation 610, the apparatus 300 includes means, such as processor 302 or the like, for determining whether the output from the machine learning model matches the known output for the selected input. To this end, identification of a match may allow for different levels of imprecision in various embodiments. For instance, depending on how closely the machine learning model is intended to fit to the set of training data, a match may only be found if the output from the machine learning model is equivalent to the known output for the selected input, or a match may be found even if there is a certain degree of mismatch between the output from the machine learning model and the known output for the selected input. In an instance in which a match is found, the procedure advances to operation 614. However, in an instance in which a match is not found, the procedure advances to operation 612.

As illustrated in operation 612, the apparatus 300 includes means, such as processor 302, memory 304, communications circuitry 306, or the like, for modifying one or more parameters of the machine learning model. To this end, machine learning model 314, as described above, may include four layers, each layer of which may perform a particular type of operation. The one or more parameters of the machine learning model may comprise coefficients or parameters of the operation performed by any of the layers of the machine learning model 314. Alternatively, the one or more parameters may comprise weights applied to one or more of the layers of the machine learning model 314. It will be understood, however, that any number of parameters may be associated with a given machine learning model and that in various embodiments any number of those parameters may be modified in operation 612. Modification of a parameter may comprise a modification to a corresponding memory location in memory 304 associated with the machine learning model. Alternatively, modification of a parameter may alternatively include transmission of a message via communications circuitry 306 to a remote device in an instance in which a remote device hosts the machine learning model being trained.

As illustrated in operation 614, the apparatus 300 includes means, such as processor 302, memory 304, communications circuitry 306, input/output circuitry 308, or the like, for determining whether to select a new record. In this regard, a new record may be selected automatically until a predetermined number of iterations have been completed of the procedure set forth in FIG. 6. Alternatively, a new record may be selected until a predetermined number of matches have been identified within a predetermined number of iterations of the procedure set forth in FIG. 6. As yet another alternative, a new record may be selected (or not) in response to receipt of an instruction from a communications circuitry 306 or input/output circuitry 308 to select (or not to select) another record. If, at operation 614, the apparatus 300 determines that a new record should be selected, the procedure returns to operation 604. Otherwise, the procedure ends.

Returning now to FIG. 4, operation 412 illustrates that the apparatus 300 further includes means, such as machine learning model 314 or the like, for producing an output in response to provision of the sequence of words to the machine learning model 314. In a broad sense, the output from the machine learning model comprises an indication of a potential conclusion that is linked-to or follows from the information contained in a larger document or set of documents. More specifically, this output may comprise an indication of one or more potential conclusions supported by the sequence of words. For instance, one potential conclusion may be an indication of whether an ICD code associated with a medical record is actually supported by the medical record. As noted above, in embodiments in which ensembling is utilized via selection of multiple different block identification operations, there will be multiple outputs produced by the machine learning model in response to inputting each of the various sequences of words created from the differently generated blocks of text. The results produced by the machine learning model at operation 412 for each of those outputs may then be used together to improve the accuracy of the identification of the one or more conclusions that follow from the information contained in the original set of text.

Regardless of the domain within which the potential conclusion(s) are identified, the output from the machine learning model may thereafter be used in a variety of ways. In some cases, the output can subsequently be used directly for a business purpose (e.g., the potential conclusion(s) regarding the record can be assumed to be correct and used to drive a subsequent business process that acts upon the potential conclusion(s)). But beyond simply being used to prompt responsive action, the process of FIG. 4 may be useful in a more granular way. For instance, the procedure of FIG. 4 may facilitate summarization of the set of text in a way that identifies which blocks in the set of text are important to the identified potential conclusion(s). Similarly, when multiple potential conclusions might be reached by various blocks in the set of text, the procedure of FIG. 4 may further facilitate identification of which blocks in the set of text support which of the multiple potential conclusions.

Figure 7:
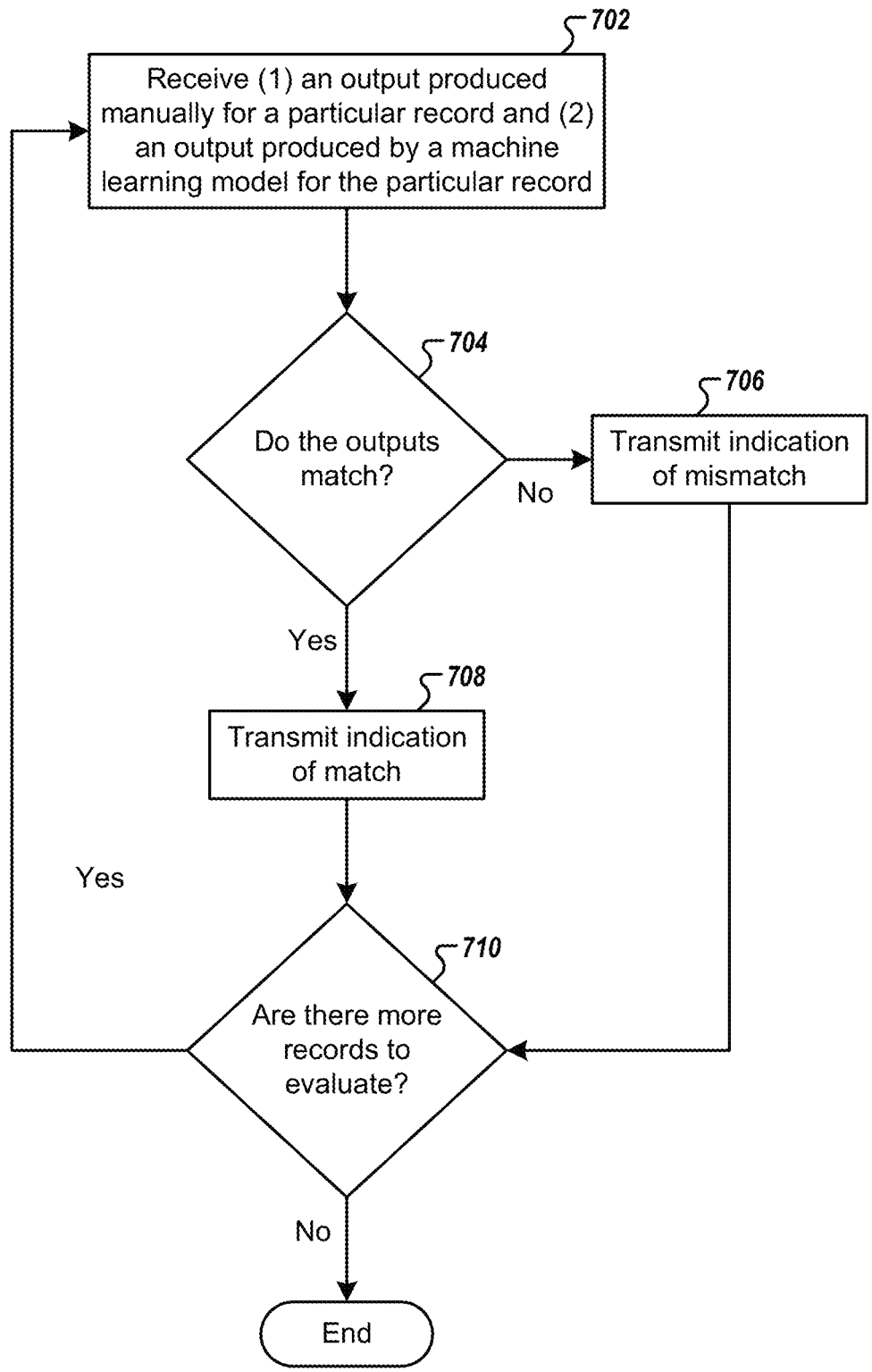
FIG. 7 illustrates a flowchart describing example operations for using the output produced from a machine learning model in a validation process, in accordance with some example embodiments described herein.

However, as shown in connection with FIG. 7 below, the output produced at operation 412 of one or more potential conclusion regarding the record need not be assumed to be correct. For instance, turning now to FIG. 7, a series of operations is shown illustrating a procedure for using the output produced from a machine learning model in a validation process. In some embodiments consistent with the procedure shown in FIG. 7, the output of the machine learning model may be used to validate the conclusions reached by a manual procedure for the same purpose. However, in other embodiments consistent with the procedure shown in FIG. 7, the potential conclusions produced by the machine learning model may be assumed to be correct, but may be validated using conclusions produced by a manual procedure that acts as a sanity check on the veracity of the automated outputs produced by the operations illustrated in FIG. 4. Either way, one example of the validation operations are illustrated in FIG. 7 and will be described in greater detail below.

As illustrated in operation 702, the apparatus 300 includes means, such as processor 302, memory 304, communications circuitry 306, input/output circuitry 308, or the like, for receiving (1) an output produced manually for a particular record and (2) an output produced by a machine learning model for the particular record. As noted above, the apparatus 300 may be a primary evaluator of records and the manual evaluator may be a validator of the work product produced by the apparatus 300. Alternatively, the manual evaluator may be a primary evaluator of records and the apparatus 300 may be a validator of the work product produced by the manual evaluator.

Either way, as illustrated in operation 704, the apparatus 300 includes means, such as processor 302 or the like, for determining if the outputs received in operation 702 match. As noted above in connection with operation 610 of FIG. 6, identification of a match may allow for different levels of imprecision in various embodiments. For instance, depending on how closely the machine learning model is intended to fit to the set of training data, a match may only be found if the output from the machine learning model is equivalent to the known output for the selected input, or a match may be found even if there is a certain degree of mismatch between the output from the machine learning model and the known output for the selected input. In an instance in which the outputs do not match, then the procedure advances to operation 706. In an instance in which the outputs match, however, then the procedure advances to operation 708.

As illustrated in operation 706, the apparatus 300 includes means, such as communications circuitry 306, input/output circuitry 308, or the like, for transmitting an indication of a mismatch in response to the determination that the output produced manually for a particular record does not match the output produced by the machine learning model for the particular record. This indication of a mismatch may trigger subsequent actions to be taken. For instance, if the apparatus 300 is a primary evaluator and the manual evaluator is a validator, then the record may be flagged for further consideration by the manual evaluator, a separate manual evaluator, or a panel of manual evaluators. If completion of that further consideration determines that the output of the apparatus 300 was incorrect, then the record may be used to further train the machine learning model of the apparatus 300 (e.g., by iteratively performing operations consistent with operations 606-612, which are above in connection with FIG. 6).

As illustrated in operation 708, the apparatus 300 includes means, such as communications circuitry 306, input/output circuitry 308, or the like, for transmitting an indication of a match in response to the determination that the output produced manually for a particular record matches the output produced by the machine learning model for the particular record. The indication of a match may constitute a validation of the output of either the apparatus 300 or the manual evaluator. In either case, however, the business process prompting the evaluation of the record may continue uninterrupted following the determination of the match. Additionally, the apparatus 300 may include means, such as memory 304 or the like, for cataloging the fact that the apparatus 300 and the manual evaluator produced matching outputs for the record, which may be evidence of increased reliability of the output of the primary evaluator.

It will be understood, however, that validation is useful for more than continued training of the apparatus 300 or sanity checking of the actions of a primary evaluator. For instance, an initial evaluation may be completed at the instruction of a first entity, and the validation may be performed at the instruction of a second entity separate from the first entity. In such situations, the validation may, in fact, be used as an audit of the initial evaluation, in which discovery of errors may be actionable. In the medical evaluation embodiment described throughout the flowchart descriptions above, the first entity may be a medical provider while the second entity may be a medical payer (e.g., an insurance company), and the use of an auditing process as described herein may facilitate the identification, by the medical payer, of claims for which there is no medical justification. In turn, this identification of improper claims may then enable the medical payer to reverse improper payments and, in turn, reduced fraud, waste, or abuse. One important use for an auditing procedure as described in connection with FIG. 7 is thus that a second entity (e.g., one party to a transaction) may be able to verify the accuracy of an evaluation undertaken by the first entity (e.g., the other party to the transaction) without undertaking the significant fixed costs associated with employing, training, and managing a staff for such a purpose. Alternatively, the second entity may still employ a staff for this auditing purpose, but may utilize the automatic validation functionality of example embodiments to focus human auditing efforts on records for which the apparatus 300 produces an output that diverges from the output proffered by the first entity. In this way, a given set of employees tasked with this auditing function may be leveraged to audit a far greater number of records by focusing their energy only on those records for which there is an indicated high likelihood of error.

More nuanced conclusions may also be reached based on the validation procedure outlined herein. For instance, when the apparatus 300 comprises a validator, a result of the performance of FIG. 7 may be useful for identifying a degree of support for the conclusion reached by the manual evaluator, even if the ultimate conclusion reached by the apparatus 300 matches the conclusion produced by the manual evaluator in the first instance. For instance, the apparatus 300 may identify the blocks in the original set of text that support the produced outcome, enabling a user to determine whether the record strongly or only weakly supports the evaluated result. In an embodiment where the apparatus 300 is used by a medical payer to audit the veracity of claims submitted by a medical payer, this additional nuance may reveal a subset of medical claims that may be incorrect.

Following determination of a match or a mismatch, operation 710 of FIG. 7 illustrates that the apparatus 300 further includes means, such as processor 302 or the like, for determining if there are more records to evaluate. There may be more records to evaluate if the operations set forth in connection with FIG. 7 are performed in a batch process (rather than being performed each time a record is evaluated by the apparatus 300). If so, then the procedure returns to operation 702 to select another record. If there are no more records to evaluate, however, then the procedure may simply end.

As described above, example embodiments provide methods and apparatuses that enable improved evaluation of records. Example embodiments thus provide tools that overcome the problems faced when evaluating records in scenarios having a low ratio of relevant to irrelevant information and where rules-based systems are not sufficiently accurate on their own. By avoiding the need to manually perform evaluations of records, example embodiments thus saves time and resources, while also eliminating the possibility of human error that has been unavoidable in the past. Moreover, embodiments described herein avoid the overhead of employing human operators to perform these tasks. Finally, by automating functionality that has historically required human analysis, the speed and consistency of the evaluations performed by example embodiments unlocks many potential new functions that have historically not been available, such as the ability to conduct near-real-time dispute resolution when conclusions drawn regarding records challenges assumptions that have previously been made regarding those records.

As these examples all illustrate, example embodiments contemplated herein provide technical solutions that solve real-world problems faced by during records evaluation. And while records evaluation has been an issue for decades, the recently exploding amount of data stored today has made this problem significantly more acute, as the demand for accurate records evaluators has grown significantly even while the complexity of evaluating those same records has itself increased.

FIGS. 4, 5, 6, and 7 illustrate flowcharts describing the operation of apparatuses, methods, and computer program products according to example embodiments of the invention. It will be understood that each block of the flowcharts, and combinations of blocks in the flowcharts, may be implemented by various means, embodied as hardware, firmware, circuitry, and/or other devices associated with execution of software including one or more software instructions. For example, one or more of the operations described above may be embodied by software instructions. In this regard, the software instructions which embody the procedures described above may be stored by a memory of an apparatus 300 employing an embodiment of the present invention and executed by a processor of the apparatus 300. As will be appreciated, any such software instructions may be loaded onto a computer or other programmable apparatus (e.g., hardware) to produce a machine, such that the resulting computer or other programmable apparatus implements the functions specified in the flowchart blocks. These software instructions may also be stored in a computer-readable memory that may direct a computer or other programmable apparatus to function in a particular manner, such that the software instructions stored in the computer-readable memory produce an article of manufacture, the execution of which implements the functions specified in the flowchart blocks. The software instructions may also be loaded onto a computer or other programmable apparatus to cause a series of operations to be performed on the computer or other programmable apparatus to produce a computer-implemented process such that the software instructions executed on the computer or other programmable apparatus provide operations for implementing the functions specified in the flowchart blocks.

The flowchart blocks support combinations of means for performing the specified functions and combinations of operations for performing the specified functions. It will be understood that one or more blocks of the flowcharts, and combinations of blocks in the flowcharts, can be implemented by special purpose hardware-based computer systems which perform the specified functions, or combinations of special purpose hardware and software instructions.

In some embodiments, some of the operations above may be modified or further amplified. Furthermore, in some embodiments, additional optional operations may be included. Modifications, amplifications, or additions to the operations above may be performed in any order and in any combination.

Example Alternative Use Case 1

Identifying Fraudulent Activity

Another relevant medical use case may be in the identification of fraudulent activity, where the apparatus 300 may evaluate medical records and claims to identify whether support exists for a particular medical claim. In such an embodiment, rather than using potential conclusions as a tool for determining the appropriateness of a payment made to a medical provider, the potential conclusions may be used to identify whether a medical claim is fraudulent in the first instance.

Example Alternative Use Case 2

Identifying Violation of Laws

Another use case may be in the identification of whether a known set of laws or regulations have been violated. For instance, the records evaluated may comprise legal documentation that is publicly available (e.g., police reports and civil and criminal court documents, or the like). A training set of legal documentation may comprise legal documentation regarding individuals or entities who have been convicted by a court of violating a law. Thus, the set of text within this training set of legal documentation may identify which blocks of text, for a current legal matter, are most closely associated with potentially violated laws. In this fashion, a version of the apparatus 300 may be designed to determine which laws are likely to have been violated in a given scenario.

Example Alternative Use Case 3

Identifying Real Property Ownership

As another example, public land records may be used to train a version of the apparatus 300 that is able to identify ownership. For instance, a training set of public land records may identify language within public land records that is most closely associated with various types of ownership statuses. For instance, clear title in a property may be closely associated with certain blocks of text, while clouds on title may be connected with other blocks of text or combinations of blocks of text. Thus, the set of text within the public land records may identify which blocks of text, for a given property, are most closely associated with various property ownership statuses. In this fashion, a version of the apparatus 300 may be designed to act as a useful heuristic for evaluating the chain of title of real property.

Example Alternative Use Case 4

Identifying Rules of Medical Necessity

As yet another example, databases of academic literature in the medical and other life sciences disciplines may be utilized to find rules of medical necessity. Rules of medical necessity set forth those activities which may be justified as reasonable, necessary, and/or appropriate, based on evidence-based clinical standards of care. By using databases of relevant academic literature, an example apparatus 300 may be designed to provide potential conclusions regarding the medical necessity of procedures undertaken in a given scenario.

CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A method for automatically auditing medical records, the method comprising:
    receiving a set of text produced from a medical record, the set of text comprising non-repeating text;
    selecting a text identification methodology from a plurality of different text identification methodologies based on historical effectiveness, the plurality of different text identification methodologies comprising an embedding layer;
    identifying, by block manipulation circuitry that uses the selected text identification methodology and from the set of text, one or more blocks of text that are related to a medical diagnosis, the one or more blocks of text consisting essentially of a proper subset of the non-repeating text;
    extracting, by the block manipulation circuitry, the one or more blocks of text;
    concatenating, by the block manipulation circuitry, the extracted one or more blocks into a sequence of words;
    inputting the sequence of words into a machine learning model; and
    in response to inputting the sequence of words into the machine learning model, producing, using the machine learning model, an indication of whether an ICD code associated with the medical record is supported by the sequence of words;
    wherein identifying the one or more blocks of the set of text that are related to a medical diagnosis comprises:

applying, by the block manipulation circuitry, the embedding layer to the set of text to identify the one or more blocks;
wherein applying the embedding layer to the set of text to identify the one or more blocks comprises:
inputting the set of text into a Word2Vec model to vectorize each block in the set of text;
inputting each ICD code description into the Word2Vec model to vectorize each ICD code description;
applying, by the block manipulation circuitry, a cosine similarity function to identify, as a high importance block, each block in the set of text whose vectorization is similar to a vectorization of an ICD code description; and
identifying, by the block manipulation circuitry, the high importance blocks of text as the one or more blocks.

2. The method of claim 1, further comprising:
receiving raw text from the medical record; and
processing, by filtration circuitry, the raw text to generate the set of text;
wherein selecting the text identification methodology comprises selecting the text identification methodology from the plurality of different text identification methodologies based on the historical effectiveness and user input, a defined selection sequence between the text identification methodologies, or a random sequence between the text identification methodologies.

3. The method of claim 2, wherein processing the raw text includes:
assigning, by the filtration circuitry, parts of speech to each word in the raw text; and
modifying, by the filtration circuitry, the raw text by:
stemming each word in the raw text; and
automatically identifying any header and footers in the raw text,
wherein the modified raw text comprises the set of text.

4. The method of claim 3, wherein automatically identifying any headers and footers in the raw text comprises:
identifying, by the filtration circuitry, identical portions of text within the raw text; and
labeling, by the filtration circuitry, the identical portions of text as header/footer text.

5. The method of claim 1, wherein the plurality of different text identification methodologies further comprises a logistic regression model and a key word analysis; and
wherein identifying the one or more blocks of the set of text that are related to a medical diagnosis comprises:
applying, by the block manipulation circuitry, the logistic regression model to the set of text to identify the one or more blocks; or
performing, by the block manipulation circuitry, the key word analysis on the set of text to identify the one or more blocks.

6. The method of claim 5, wherein identifying the one or more blocks of the set of text that are related to a medical diagnosis comprises:
applying, by the block manipulation circuitry, the logistic regression model to the set of text to identify the one or more blocks;
wherein applying the logistic regression model to the set of text to identify the one or more blocks comprises:
inputting the set of text into a logistic regression model that produces an indication of high importance blocks in the set of text; and
identifying, by the block manipulation circuitry, the high importance blocks as the one or more blocks.

7. The method of claim 5, wherein identifying the one or more blocks of the set of text that are related to a medical diagnosis comprises:
performing, by the block manipulation circuitry, the key word analysis on the set of text to identify the one or more blocks;
wherein performing the key word analysis on the set to identify the one or more blocks comprises:
identifying, by the block manipulation circuitry, occurrence of key words corresponding to the ICD code descriptions within each block in the set of text to identify high importance blocks in the set of text; and
identifying, by the block manipulation circuitry, the high importance blocks as the one or more blocks.

8. The method of claim 1, wherein the machine learning model comprises a deep learning model having a plurality of layers.

9. The method of claim 8, wherein the plurality of layers comprise:
the embedding layer configured to vectorize each word in the sequence of words;
a convolutional layer configured to extract patterns between the vectorized words in the sequence of words;
a recurrent neural network (RNN) layer configured to relate words that appear earlier in the sequence of words to words that appear later in the sequence of words; and
a classification layer configured to determine whether the ICD code associated with the medical record is supported by the sequence of words.

10. The method of claim 1, further comprising:
in an instance in which the ICD code associated with the medical record is not supported by the sequence of words, generating, by communications circuitry, an alert to prompt human intervention.

11. An apparatus for automatically auditing medical records, the apparatus comprising:
block manipulation circuitry configured to:
receive a set of text produced from a medical record, the set of text comprising non-repeating text,
select a text identification methodology from a plurality of different text identification methodologies based on historical effectiveness, the plurality of different text identification methodologies comprising an embedding layer;
identify using the selected text identification methodology, from the set of text, one or more blocks of text that are related to a medical diagnosis, the one or more blocks of text consisting essentially of a proper subset of the non-repeating text,
extract the one or more blocks of text, and
concatenate the extracted one or more blocks into a sequence of words; and
a machine learning model configured to, in response to inputting the sequence of words into the machine learning model, produce an indication of whether an ICD code associated with the medical record is supported by the sequence of words;
wherein the block manipulation circuitry is configured to identify the one or more blocks of the set of text that are related to the medical diagnosis by:
applying the embedding layer to the set of text to identify the one or more blocks;
wherein applying the embedding layer to the set of text to identify the one or more blocks comprises:
inputting the set of text into a Word2Vec model to vectorize each block in the set of text;

inputting each ICD code description into the Word2Vec model to vectorize each ICD code description;
applying a cosine similarity function to identify, as a high importance block, each block in the set of text whose vectorization is similar to a vectorization of an ICD code description; and
identifying the high importance blocks of text as the one or more blocks.

12. The apparatus of claim 11, further comprising filtration circuitry configured to:
receive raw text from the medical record;
assign parts of speech to each word in the raw text; and
modify the raw text by:
stemming each word in the raw text; and
automatically identifying any header and footers in the raw text by
identifying identical portions of text within the raw text; and
labeling the identical portions of text as header/footer text;
wherein the modified raw text comprises the set of text; and
wherein the block manipulation circuitry is further configured to select the text identification methodology comprises by selecting the text identification methodology from the plurality of different text identification methodologies based on the historical effectiveness and user input, a defined selection sequence between the text identification methodologies, or a random sequence between the text identification methodologies.

13. The apparatus of claim 11, wherein the plurality of different text identification methodologies further comprises a logistic regression model and a key word analysis; and
wherein the block manipulation circuitry is configured to identify the one or more blocks of the set of text that are related to a medical diagnosis by:
applying the logistic regression model to the set of text to identify the one or more blocks; or
performing the key word analysis on the set to identify the one or more blocks.

14. The apparatus of claim 13, wherein the block manipulation circuitry is configured to identify the one or more blocks of the set of text that are related to the medical diagnosis by:
applying the logistic regression model to the set of text to identify the one or more blocks;
wherein applying the logistic regression model to the set of text to identify the one or more blocks comprises:
inputting the set of text into a logistic regression model that produces an indication of high importance blocks in the set of text; and
identifying the high importance blocks as the one or more blocks.

15. The apparatus of claim 13, wherein the block manipulation circuitry is configured to identify the one or more blocks of the set of text that are related to the medical diagnosis by:
performing the key word analysis on the set to identify the one or more blocks;
wherein performing the key word analysis on the set to identify the one or more blocks comprises:
identifying occurrence of key words corresponding to the ICD code descriptions within each block in the set of text to identify high importance blocks in the set of text; and
identifying the high importance blocks as the one or more blocks.

16. The apparatus of claim 11, wherein the machine learning model comprises a deep learning model having a plurality of layers, the plurality of layers comprising:
the embedding layer configured to vectorize each word in the sequence of words;
a convolutional layer configured to extract patterns between the vectorized words in the sequence of words;
a recurrent neural network (RNN) layer configured to relate words that appear earlier in the sequence of words to words that appear later in the sequence of words; and
a classification layer configured to determine whether the ICD code associated with the medical record is supported by the sequence of words.

17. The apparatus of claim 11, further comprising communications circuitry configured to:
in an instance in which the ICD code associated with the medical record is not supported by the sequence of words, generate an alert to prompt human intervention.

18. A computer program product comprising at least one non-transitory computer-readable storage medium for automatically auditing medical records, the at least one non-transitory computer-readable storage medium storing software instructions that, when executed, cause an apparatus to perform operations comprising:
receive a set of text produced from a medical record, the set of text comprising non-repeating text;
select a text identification methodology from a plurality of different text identification methodologies based on historical effectiveness, the plurality of different text identification methodologies comprising a logistic regression model, a key word analysis, and an embedding layer;
identify using the selected text identification methodology, from the set of text, one or more blocks of text that are related to a medical diagnosis, the one or more blocks of text consisting essentially of a proper subset of the non-repeating text;
extract the one or more blocks of text;
concatenate the extracted one or more blocks into a sequence of words;
input the sequence of words into a machine learning model; and
in response to inputting the sequence of words into the machine learning model, produce, using the machine learning model, an indication of whether an ICD code associated with the medical record is supported by the sequence of words;
wherein identifying the one or more blocks of the set of text that are related to the medical diagnosis comprises:
applying the embedding layer to the set of text to identify the one or more blocks;
wherein applying the embedding layer to the set of text to identify the one or more blocks comprises:
inputting the set of text into a Word2Vec model to vectorize each block in the set of text;
inputting each ICD code description into the Word2Vec model to vectorize each ICD code description;
applying a cosine similarity function to identify, as a high importance block, each block in the set of text whose vectorization is similar to a vectorization of an ICD code description; and identifying the high importance blocks of text as the one or more blocks.

* * * * *